(12) United States Patent
Dubnov et al.

(10) Patent No.: US 7,734,350 B2
(45) Date of Patent: Jun. 8, 2010

(54) RESPIRATION APPARATUS

(75) Inventors: Boris Dubnov, Petach-Tiquwa (IL); Mordehai Tessel, Kfar-Saba (IL)

(73) Assignee: Zmed Technologies, Inc., Bellaire, TX (US)

( * ) Notice: Subject to any disclaimer, the term of this patent is extended or adjusted under 35 U.S.C. 154(b) by 752 days.

(21) Appl. No.: 11/424,011

(22) Filed: Jun. 14, 2006

(65) Prior Publication Data
US 2007/0293907 A1 Dec. 20, 2007

(51) Int. Cl.
*A61N 1/00* (2006.01)
(52) U.S. Cl. ......................................... 607/42
(58) Field of Classification Search .................. 607/42, 607/55–57; 381/312–331
See application file for complete search history.

(56) References Cited

U.S. PATENT DOCUMENTS

| | | | |
|---|---|---|---|
| 3,802,417 A | 4/1974 | Lang | |
| 3,998,209 A | 12/1976 | Macvaugh | |
| 4,064,869 A | 12/1977 | Defares et al. | |
| 4,146,885 A | 3/1979 | Lawson, Jr. | |
| 4,644,330 A | 2/1987 | Dowling | |
| 4,657,026 A | 4/1987 | Tagg | |
| 4,715,367 A | 12/1987 | Crossley | |
| 4,788,533 A | 11/1988 | Mequignon | |
| 4,813,427 A | 3/1989 | Schlaefke et al. | |
| 5,178,156 A * | 1/1993 | Takishima et al. | 600/537 |
| 5,295,490 A | 3/1994 | Dodakian | |
| 5,477,867 A | 12/1995 | Balkanyi | |
| 5,645,054 A | 7/1997 | Cotner et al. | |
| 5,853,005 A | 12/1998 | Scanlon | |
| 6,093,158 A | 7/2000 | Morris | |
| 6,142,950 A | 11/2000 | Allen et al. | |
| 6,155,985 A | 12/2000 | Ruton | |
| 6,190,328 B1 | 2/2001 | Ruton et al. | |
| 6,213,955 B1 | 4/2001 | Karakasoglu et al. | |
| 6,314,324 B1 * | 11/2001 | Lattner et al. | 607/42 |
| 6,329,352 B1 | 12/2001 | Meyer et al. | |
| 6,368,287 B1 | 4/2002 | Hadas | |

(Continued)

FOREIGN PATENT DOCUMENTS

WO 8704630 A1 8/1987

OTHER PUBLICATIONS

Carley, D. W. et al., "Respiratory and Arousal Responses to Acoustic Stimulation." Chest. 112(6): 1567-1571, 1997.

(Continued)

*Primary Examiner*—Mark W Bockelman
*Assistant Examiner*—Roland Dinga
(74) *Attorney, Agent, or Firm*—Haynes and Boone LLP

(57) ABSTRACT

The present invention generally relates to an apparatus and method for stimulating respiration during sleep. In one aspect, a respiration stimulation system is provided. The respiration stimulation system includes a detector configured to measure a respiratory cycle or a user and provide an electrical output signal indicative of the respiratory cycle. The respiration stimulation system further includes a control device configured to receive the electrical output signal from the detector and monitor the respiratory cycle of the user. Additionally, the respiration stimulation system includes a stimulator configured to apply stimuli to at least one point of stimulation upon receipt of a signal from the control device. In another aspect, a method of stimulating respiration in a user is provided. In a further aspect, a respiration stimulation system is provided.

10 Claims, 2 Drawing Sheets

U.S. PATENT DOCUMENTS

| | | |
|---|---|---|
| 6,544,199 B1 | 4/2003 | Morris |
| 6,748,275 B2 * | 6/2004 | Lattner et al. .................. 607/42 |
| 6,928,324 B2 * | 8/2005 | Park et al. ..................... 607/20 |
| 6,935,335 B1 | 8/2005 | Lehrman et al. |
| 6,989,744 B2 | 1/2006 | Proebsting |
| 7,025,729 B2 | 4/2006 | de Chazal et al. |
| 7,115,097 B2 | 10/2006 | Johnson |
| 2003/0195588 A1 | 10/2003 | Fischell et al. |
| 2003/0199945 A1 | 10/2003 | Ciulla |
| 2005/0197588 A1 | 9/2005 | Freeberg |
| 2005/0274387 A1 | 12/2005 | MacKen |
| 2005/0277821 A1 | 12/2005 | Payne, Jr. |
| 2005/0279367 A1 * | 12/2005 | Klemperer .................. 128/861 |
| 2005/0283039 A1 | 12/2005 | Cornel |
| 2005/0283089 A1 | 12/2005 | Sullivan et al. |
| 2006/0102171 A1 | 5/2006 | Gavish |
| 2006/0145878 A1 | 7/2006 | Lehrman et al. |
| 2006/0173257 A1 | 8/2006 | Nagai et al. |
| 2006/0174897 A1 | 8/2006 | Sarkisian |
| 2006/0187067 A1 | 8/2006 | Simpson |
| 2006/0206014 A1 | 9/2006 | Ariav |

OTHER PUBLICATIONS

Basner, R.C. et al., Effect of Induced Transient Arousal on Obstructive Apnea Duration. J. Appl. Physiol. 78(4): 1469-1476, 1995.

Carlson, D.M. et al., Acoustically Induced Cortical Arousal Increases Phasic Pharyngeal Muscle and Disphragmatic EMG in NREM Sleep. J. Appl. Physiol. 76(4): 1553-9, 1994.

Khoo, Michael C. K. et al., "Ventilatory Dynamics During Transient Arousal from NREM Sleep: Implications for Respiratory Control Stability." J. Appl. Physiol. 80(5): 1475-84, 1996.

Badr, M. Safwan et al., "Ventilatory Response to Induced Auditory Arousals During NREM Sleep." Sleep. 20(9): 707-14, 1997.

Schwartz, D.J. and Moxley, P. "On the Potential Clinical Relevance of the Length of Arousals from Sleep in Patients with Obstructive Sleep Apnea." J. Clin. Sleep Med. 2(2): 175-80, 2006.

Pressler, G.A. et al., "Detection of Respiratory Sounds at the External Ear." IEEE Transactions on Biomedical Engineering. 51(12): 2089-96, 2004. (Abstract Only).

Kingshott, R.N. et al., "Does Arousal Frequency Predict Daytime Function." Eur Respir J. 12; 1264-1270, 1988.

Stepanski, E.J. "The Effect of Sleep Fragmentation on Daytime Function." Sleep. 25(3): 268-276, 2002.

Stradling, J.R. et al., "Prevalence of sleepiness and its relation to autonomic evidence of arousals and increase aspiratory effort in a community based population of men and women." J Slleep Res. 9; 381-388, 2000.

* cited by examiner

RESPIRATION APPARATUS

BACKGROUND OF THE INVENTION

1. Field of the Invention

Embodiments of the present invention generally relate to respiration. More specifically, the present invention relates to an apparatus and method for stimulating respiration during sleep.

2. Description of the Related Art

A clinical pathologic entity called Sleep Apnea syndrome (SAS) affects many individuals around the world. Sleep apnea means "cessation of breath." It is characterized by repetitive stops of respiration, each lasting for more than about 10 seconds, which brings the brain into a hypoxic state (reduced arterial oxygen tension). SAS may cause severe disturbances of sleep itself and may have deleterious effects on mental activities, such as intellectual performance, memory, and behavior. Further, SAS is known as one of the causes of cardiovascular diseases, increased blood pressure (hypertension), stroke, heart arrhythmia, and conduction disturbances which may lead even to fatal cardiac arrest. SAS is especially dangerous in patents having chronic lung and heart diseases.

Many patients are at risk of suffering from SAS. Certain populations of patients are at higher risk than others. For instance, 30% of the middle-aged population, mainly men, suffers from respiratory disturbances during sleep. Additionally, frequent sleep apneas are found in about 50% of cardiovascular patients. Furthermore, there are many more patients with "unrecognized" SAS, since only direct observation of the respiratory cycle of a patient during sleep can reveal this pathology.

There are essentially two main types of apnea. One type relates to stops in respiration during sleep caused by cessation or reduction of nerve stimuli extending from the respiratory center in the brain to respiratory muscles. This type of apnea is commonly referred to as central apnea. The second type of apnea relates to the uncontrolled excessive decrease of muscle tone in the upper airway resulting in obstruction. This type of apnea is commonly referred to as obstructive apnea. The incomplete obstruction of the upper airway usually causes snoring. Frequently, patients have a combination of central and obstructive apneas, which is referred to as mixed apnea.

Obstructive apnea is caused by the abnormal, excessive reduction of muscle tone of the oropharynx, pharynx, and hypopharynx; the retraction of the tongue; and negative pressure in nasal space which independently or collectively can result in the collapse and obstruction of the upper airway. Generally, the oropharyngeal muscles maintain the upper airway passage open in order to allow a normal breathing. As such, the reduction of muscle tone of oropharyngeal muscles is one of the main mechanisms of SAS.

A common means of protection against SAS is usually arousal from the sleep and restoration of normal breathing as a result of temporary normalization of the cortical neural control of respiration. However, as expected, these repetitive arousals result in fragmented disturbed sleep.

Current treatments of SAS have been limited to mechanical stenting of the airway via CPAP (continuous positive airway pressure) devices and oral appliances; and surgical procedures aimed at removing, reducing, repositioning, or stiffening tissue in the upper airway. CPAP and oral devices have a 50%-60% compliance rate because of patients' feelings of claustrophobia, nasal stuffiness, and inconvenience related to these devices' awkward and cumbersome equipment. Surgical treatments are usually very painful, require the use of general anesthesia, and can have severe complications. In the medical literature, surgical interventions are at best 60-70% effective at curing sleep apnea.

The most widely used device is the CPAP, which prevents collapse of the pharynx by blowing air into the upper airway tract. However, the CPAP device has several substantial shortcomings. For instance, the CPAP device tends to be uncomfortable and noisy. Further, the CPAP device requires the use of a mask on the face of the patient, preventing free movement during sleep. Additionally, the inflow of the air pressure during the use of the CPAP device sometimes causes the sensation of suffocation, nasal drying, and even pain in the ears due to barotrauma. Furthermore, the regulation and tuning of the CPAP device requires time and observation. As a result, patient compliance is the greatest hurdle with the CPAP device and the CPAP device rarely gets above a 60% compliance rate.

Therefore, there remains a need for a device to aid in the restoration of normal breathing to SAS patients that is simple to use, comfortable, non-invasive, painless, and does not cause the sensation of suffocation or nasal drying.

SUMMARY OF THE INVENTION

The present invention generally relates to an apparatus and method for stimulating respiration during sleep. In one aspect, a respiration stimulation system is provided. The respiration stimulation system includes a detector configured to measure a respiratory cycle of a user and provide an electrical output signal indicative of the respiratory cycle. The respiration stimulation system further includes a control device configured to receive the electrical output signal from the detector and monitor the respiratory cycle of the user. Additionally, the respiration stimulation system includes a stimulator configured to apply stimuli to at least one point of stimulation upon receipt of a signal from the control device.

In another aspect, a method of stimulating respiration in a user is provided. The method includes detecting a respiratory cycle of the user and monitoring the respiratory cycle of the user. The method further includes applying acoustic stimulation upon detection of an error in the respiratory cycle of the user in order to stimulate respiration.

In a further aspect, a method of stimulating respiration in a user is provided. The method includes detecting a respiratory cycle of the user and monitoring the respiratory cycle of the user. The method further includes applying a puff of air to at least one point of stimulation upon detection of an error in the respiratory cycle of the user in order to stimulate respiration.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

In general, the present invention relates to an apparatus and method for stimulating respiration during sleep. With specific reference now to the figures in detail, it is stressed that the particulars shown are by way of example and for purposes of illustrative discussion of the embodiments of the present invention only. In this regard, no attempt is made to show structural details of the invention in more detail than is necessary for a fundamental understanding of the invention.

Figure 1:
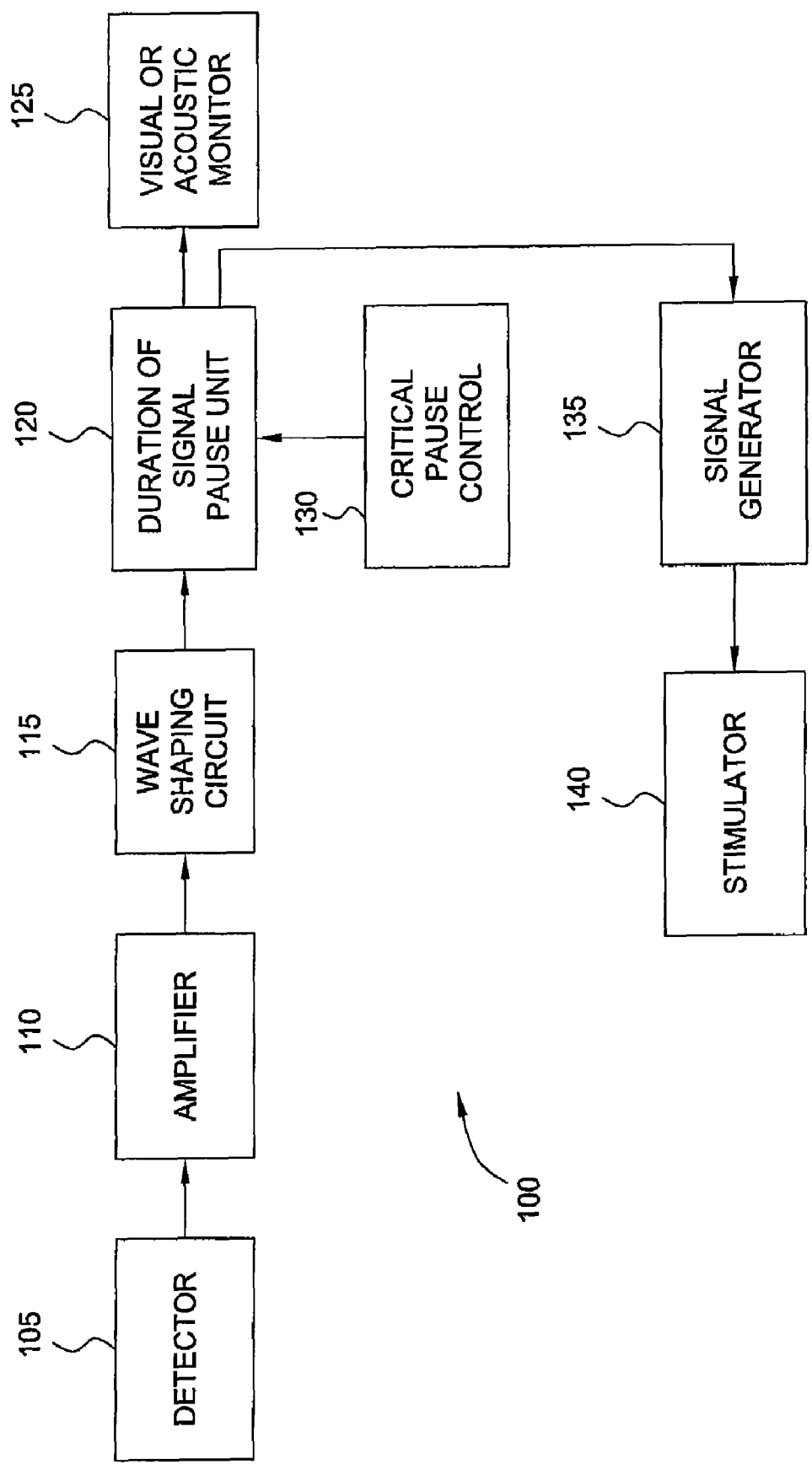
FIG. 1 illustrates a block diagram of a device for acoustic stimulation of respiration.

FIG. 1 illustrates a block diagram of a device 100 for acoustic stimulation of respiration in accordance to the present invention. As illustrated in FIG. 1, the device 100 includes a sensor or detector 105. Generally, the detector 105 is configured to measure the respiratory cycle of a user and then provide an electrical output signal indicative of the respiratory cycle. The detector 105 is made to be removably affixed to the user. In one embodiment, the detector 105 is an air-flow detector which is affixable in or adjacent to the nose or mouth of the user. In another embodiment, the detector 105 is a rib-cage movement detector designed to be affixed across the torso of the user and to provide an output signal whenever the rib-cage expands or contracts during breathing. In another embodiment, the detector 105 may measure blood parameters of the user, such as the percentage of oxygen in the blood stream. It should be understood, however, that the detector 105 can be any type of mechanism capable of measuring the respiratory cycle of a user and providing an electrical output signal indicative of the respiratory cycle of the user, without departing from principles of the present invention.

Figure 2:
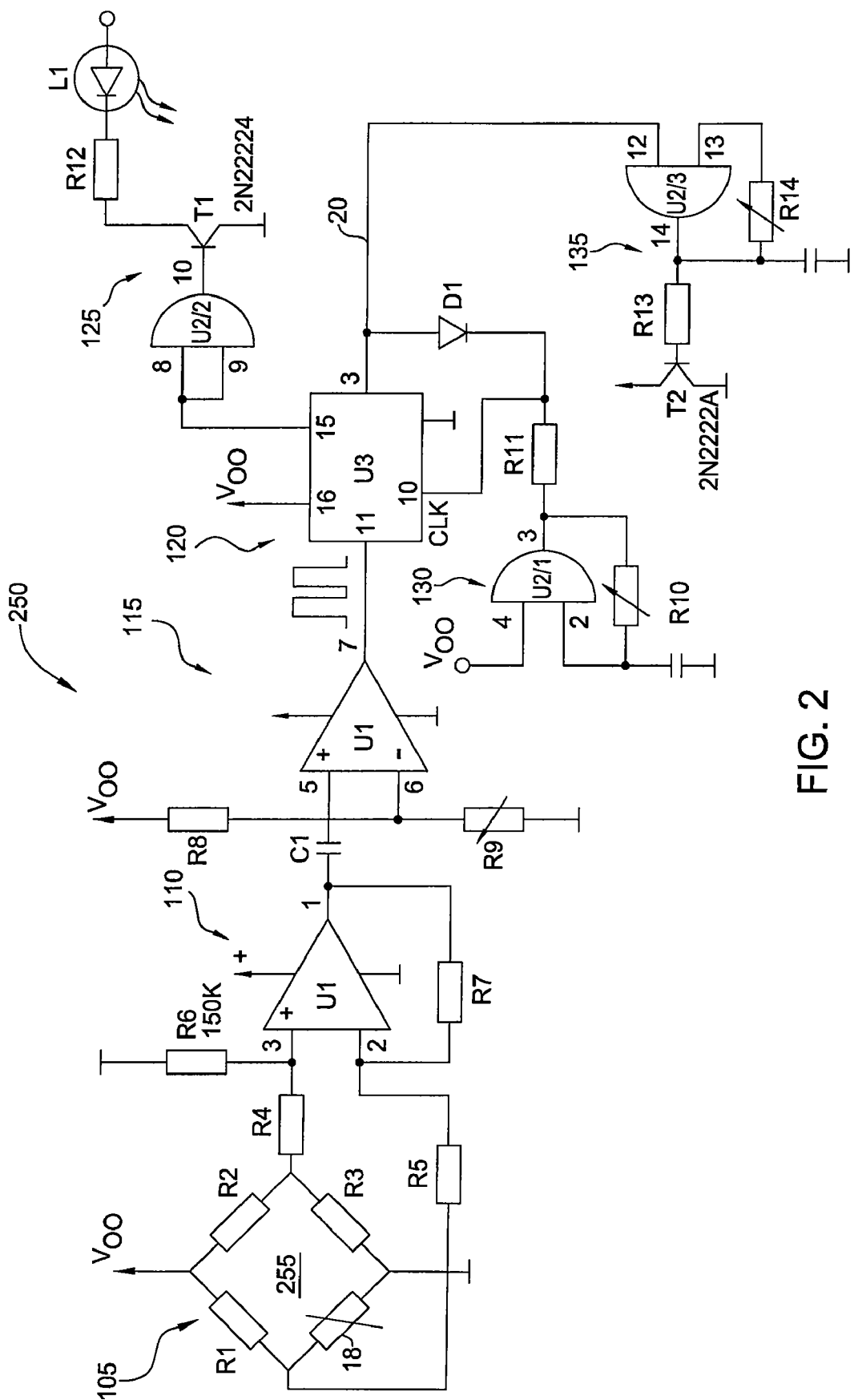
FIG. 2 illustrates a circuit diagram of the device in accordance with the present invention.

The output signal produced by the detector 105 is sent to a control device. Generally, the control device is a device that is capable of receiving a signal from the detector 105, analyzing the signal and then sending a signal to a stimulator 140. In one embodiment, the control device may include an amplifier 110, a wave shaping circuit 115, a pause unit 120, a monitor 125, a critical pause control circuit 130, a signal generator 135 as illustrated in FIGS. 1 and 2. It should be understood, however, that the control device is not limited to this embodiment. Rather, the control device may be any type of device known in the art that is capable of receiving a signal from the detector 105, analyzing the signal and then sending a signal to the stimulator 140, without departing from principles of the present invention. For instance, in another embodiment, the control device or any other component of the device 100 is an integrated circuit. In a further embodiment, the control device or any other component of the device 100 is a central processing unit (CPU). It should be further noted that the detector 105 and/or the stimulator 140 may comprise a central processing unit (CPU) and/or an integrated circuit.

The output signal produced by the detector 105 is amplified by an amplifier 110 and then sent to a wave shaping circuit 115. The circuit 115 is configured to change the signal into a shaped signal, such as a square wave, which is indicative of the user respiratory cycle. Thereafter, the shaped signal is sent to a pause unit 120 for monitoring. Generally, the pause unit 120 is used to measure the duration between adjacent output signals generated by the circuit 115 or conversely, the duration of signal pause between consecutive output signals or pulses. During normal breathing, a visual and/or an audible signal may be present in a monitor 125. Upon cessation of respiration for a period exceeding a predetermined period of time, the signal from the monitor 125 may be altered.

The pause unit 120 also receives signals of adjustable durations from a critical pause control circuit 130. These signals are used by the pause unit 120 for determining whether the duration between consecutive output signals generated by the circuit 115 has exceeded a preset period of time. If the preset period of time, such as 10 seconds, has been exceeded, the pause unit 120 activates a signal generator 135 which, in turn, operates a respiration stimulator 140 constructed and arranged to restore normal breathing of the user. Essentially, the stimulator 140 is configured to apply stimuli or send signals (electrical, mechanical, or acoustic) to one or several points of stimulation in order to restore normal breathing of the user. The points of stimulation may be the tympanic membrane, acoustic nerve, cerebral cortex muscles of the nasopharynx, and the nasal mucosal receptors.

FIG. 2 illustrates a circuit diagram 250 of the device 100 in accordance with the present invention. As shown, the detector 105 includes a thermistor 255 arranged in a bridge circuit having resistors $R_1$, $R_2$, and $R_3$. During a breathing cycle of the user, air-flow impinging on the thermistor 255 changes its resistance and thus unbalancing the bridge. Thereafter, current flowing through resistors $R_4$ and $R_5$ will be amplified by the amplifier 110 and an oscillatory signal corresponding to the breathing cycle will be sent from the amplifier 110 via an output terminal 1.

The oscillatory signal corresponding to the breathing cycle is passed via capacitor C1 to the wave shaping circuit 115 consisting of the unit $U_1$, resistor $R_8$, and variable resistor $R_9$. The shaped waveform at the output of the unit $U_1$ is thus applied to terminal 11 of a counter $U_3$. Each incoming pulse resets the counter $U_3$. Simultaneously, the control circuit 130, including the unit $U_{2/1}$ and the potentiometer $R_{10}$, generates pulses or signals relating to the preset period of time, while the control circuit 130 applies the pulses via resistor $R_{11}$ to the clock terminal 10 of the counter $U_3$. The latter counts the number of pulses which are applied. If within a period of time, set by the resistor $R_9$ of the shaping circuit 115, a reset pulse is not applied to the counter pause unit 120, there appears on its output terminal 3 an output signal. The output signal is applied, via lead 20 to the signal generator 135 which includes the unit $U_{2/3}$, the resistor $R_{12}$, the power transistor $T_2$, and the potentiometer $R_{14}$. The generator 135 forms a signal which is applied via resistor $R_{13}$ to the base of the transistor $T_2$.

The transistor $T_2$ conducts and activates the stimulator 140 as discussed herein. As long as a signal appears on terminal 3 of $U_3$, the diode $D_1$ prevents the arrival of stimuli from the control circuit 130 to the terminal 10 of $U_3$. This state of the unit $U_3$ will prevail until a reset signal initiated by the restoration of breathing arrives at terminal 11 of the unit. The visual and/or acoustic monitor 125 receives activating signals from terminal 15 of the unit $U_3$. These signals are passed via unit $U_{2/2}$, transistor $T_1$, and resistor $R_{12}$ to the light emitting-device (LED) $L_1$. The latter is set to flicker during a normal breathing operation. The device may be powered by any suitable power source, such as a battery.

In another embodiment, a detector unit registers an alteration in breathing and generated an impulse to a stimulating unit. This stimulating unit then delivers a controlled and intermittent puff of air to at least one point of stimulation which may include but is not limited to the facial, nasal and/or nasopharyngeal skin lining or mucosa. This will result in a physiologic response known as the face blow reflex. The patient will respond with a normal physiologic inspiration.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

While the foregoing is directed to embodiments of the present invention, other and further embodiments of the invention may be devised without departing from the basic scope thereof, and the scope thereof is determined by the claims that follow.

The invention claimed is:

1. A respiration stimulation apparatus for use during sleep, comprising:
 a detector configured to measure a respiratory cycle of a user during sleep and provide an output signal indicative of the respiratory cycle;
 a control device in communication with the detector, the control device receiving the output signal from the detector to monitor the respiratory cycle of the user, the control device comprising:
  an amplifier that amplifies the output signal received from the detector;
  a wave shaping circuit in communication with the amplifier, the wave shaping circuit changing the amplified output signal into a shaped signal indicative of the respiratory cycle; and
  a pause unit in communication with the wave shaping circuit, the pause unit analyzing the shaped signal received from the wave shaping circuit to determine a duration of the respiratory cycle and comparing the determined duration of the respiratory cycle to a preset period of time, if the determined duration exceeds the preset period of time then the pause unit activates a signal generator in communication with the pause unit; and
 a stimulator in communication with signal generator, the stimulator configured to apply an audible acoustic stimulus to an acoustic nerve of the user upon receipt of the signal from the signal generator during sleep.

2. The respiration stimulation apparatus of claim 1, wherein the stimulator is configured to stop applying the acoustic stimuli when the control device determines that respiration has been restored.

3. The respiration stimulation apparatus of claim 1, wherein the pause unit is in communication with a pause control circuit, the pause control circuit providing a control signal indicative of the preset period of time to the pause unit.

4. the respiration stimulation apparatus of claim 3, wherein the preset period of time is adjustable.

5. The respiration stimulation apparatus of claim 1, wherein acoustic stimulus applied by the stimulator is variable.

6. The respiration stimulation apparatus of claim 1, wherein the detector is sized and shaped for placement adjacent to or within a nose of the user.

7. The respiration stimulation apparatus of claim 1, wherein at least one of the detector, the control device, and the stimulator comprises an integrated circuit or a central processing unit (CPU).

8. The respiration stimulation apparatus of claim 7, wherein the stimulator is configured to stop applying the acoustic stimuli when the control device determines that respiration has been restored.

9. A respiration stimulation apparatus for use during sleep, comprising:
 a detector sized and shaped for placement adjacent to or within a nose of a user, the detector configured to measure a respiratory cycle of the user during sleep and provide an output signal indicative of the respiratory cycle;
 a control device in communication with the detector, the control device receiving the output signal from the detector in order to monitor the respiratory cycle of the user during sleep, the control device comprising:
  an amplifier that amplifies the output signal received from the detector;
  a wave shaping circuit in communication with the amplifier, the wave shaping circuit converting the amplified output signal into a shaped signal indicative of the respiratory cycle; and
  a pause unit in communication with the wave shaping circuit, the pause unit analyzing the shaped received from the wave shaping circuit to determine a duration of the respiratory cycle and comparing the determined duration of the respiratory cycle to a preset period of time as defined by a signal received from a pause control circuit;
  wherein the control device emits an activation signal when the determined duration of the respiratory cycle exceeds the preset period of time defined by the signal received from the pause control circuit; and
 a stimulator in communication with control device, the stimulator configured to apply an acoustic stimulus to an acoustic nerve of the user receipt of the activation signal from the control device.

10. The respiration stimulation apparatus of claim 9, wherein the preset period of time is adjustable.

* * * * *